(12) United States Patent
Davenport

(10) Patent No.: US 6,318,366 B1
(45) Date of Patent: Nov. 20, 2001

(54) SUPPLY VALVE AND DIAPHRAGM FOR A PNEUMATICALLY-OPERATED GAS DEMAND APPARATUS

(75) Inventor: James M. Davenport, Fallbrook, CA (US)

(73) Assignee: Salter Labs, Arvin, CA (US)

(*) Notice: Subject to any disclaimer, the term of this patent is extended or adjusted under 35 U.S.C. 154(b) by 0 days.

(21) Appl. No.: 09/405,419

(22) Filed: Sep. 22, 1999

(51) Int. Cl.$^7$ .................................................. A62B 9/02
(52) U.S. Cl. .................................. 128/205.24; 128/204.18
(58) Field of Search ........................ 128/200.14, 200.24, 128/201.28, 203.12, 203.24, 204.18, 204.26, 205.24, 207.12; 137/115.03, 171, 504, 510, 843, 855, 908

(56) References Cited

U.S. PATENT DOCUMENTS

| | | |
|---|---|---|
| 2,615,463 | * 10/1952 | Burns .............................. 128/205.24 |
| 5,360,000 | 11/1994 | Carter . |
| 5,666,945 | 9/1997 | Davenport . |
| 6,098,622 | * 8/2000 | Nobile et al. .................. 128/205.24 |

* cited by examiner

*Primary Examiner*—Glenn K. Dawson
(74) *Attorney, Agent, or Firm*—Klehr, Harrison; John F. Letchford (57) ABSTRACT

A supply valve for a pneumatically-operated gas demand apparatus or an intermittent gas delivery device disposed between a source of pressurized respiratory gas and a patient. The valve includes first and second housing parts defining a chamber and having first and second cooperating fluid passageways. A flexible diaphragm member is disposed in the chamber. The diaphragm member includes a central sealing portion and a radial projection integral with the central sealing portion for enabling fluid communication between the first and second fluid passageways and for sealing the first and second passageways against leakage.

8 Claims, 5 Drawing Sheets

SUPPLY VALVE AND DIAPHRAGM FOR A PNEUMATICALLY-OPERATED GAS DEMAND APPARATUS

FIELD OF THE INVENTION

The present invention relates generally to respiratory equipment and, in particular, to a supply valve and diaphragm for a pneumatically-operated gas demand apparatus of a type which is coupled in interruptible fluid communication between a recipient and at least one source of a pressurized gas and which is adapted for controlling delivery of the pressurized gas to the recipient as the recipient inhales and exhales.

BACKGROUND OF THE INVENTION

Many medical patients suffering from any one of a variety of lung ailments are often prescribed supplemental oxygen therapy so that the patient could breath oxygen-enriched air throughout the day and sometimes throughout the night. Earlier supplemental oxygen therapy employed a nasal cannula system operably connected between a tank of compressed oxygen and the patient's nose. Oxygen was continuously delivered to the patient throughout the patient's entire breathing cycle. This method of continuously delivering oxygen to the patient throughout the patient's breathing cycle was considered wasteful because much of the oxygen dissipated into the ambient air environment. Better methods of delivering oxygen to the patient were later developed which included improved equipment that would only deliver oxygen to the patient during the inhalation phase of the patient's breathing cycle. Usually, this improved equipment employed a demand valve which opened to deliver supplemental oxygen to the patient only when the patient inhaled. Numerous types of demand valves are well known in the prior art.

One such demand valve is described in U.S. Pat. No. 5,360,000 to Carter. This demand valve is compact, simplified and totally pneumatic. The demand valve which is coupled between a source of pressurized gas such as oxygen and the patient includes a valve body having a gas flow passageway and pneumatically-coupled sensing and slave diaphragms. The slave diaphragm is interposed in the gas flow passageway and prevents gas from flowing during the exhalation phase of the patient's respiratory cycle. During inhalation, which is sensed by a sensing diaphragm, the slave diaphragm moves to open the gas flow passageway, thus permitting flow of gas to the patient.

U.S. Pat. No. 5,666,945 to Davenport, the disclosure of which is incorporated herein by reference, describes a pneumatically-operated gas demand apparatus which overcomes many of the deficiencies of prior devices. The Davenport apparatus includes cooperating supply and sensing valves in interruptible fluid communication between a recipient (or patient) and at least a first source of pressurized gas. The supply valve includes a supply valve housing with a first diaphragm member disposed therein. Similarly, the sensing valve includes a sensing valve housing and a second diaphragm member disposed therein. The Davenport apparatus is constructed such that, when recipient inhales, the second diaphragm member assumes a flow-causing position and the first diaphragm member assumes a flow-supplying position whereby pressurized respiratory gas is delivered to the recipient. When the recipient exhales, the second diaphragm member assumes a flow-stopping position and the first diaphragm member assumes a flow-blocking position, thereby preventing delivery of the respiratory gas to the recipient.

The Davenport apparatus performs its intended functions quite effectively. However, its supply (or pilot) valve is somewhat complicated in design, labor-intensive in construction and susceptible to gas leaks. The supply valve housing comprises first and second housing parts including cooperating passageways for providing fluid communication between the supply valve and the sensing valve. As presently constructed, both the first and second housing parts must be drilled or bored to create portions of a first of the passageways. An O-ring or similar sealing means must be provided at the juncture of the first passageway portions in order to prevent respiratory gas leakage from between the first and second housing parts. At least one of the first and second housing parts must also be counterbored to accommodate the O-ring. The second housing part is radially drilled or bored to produce a second passageway which intersects the first passageway. After formation, the second passageway must be plugged or otherwise sealed from the ambient atmosphere. So constructed, the plug represents another site from, through or around which respiratory gas may leak from the valve housing. The many construction steps of the Davenport supply valve, coupled with its potential for gas leakage at more than one site, render the valve somewhat onerous to assemble and less than optimal from a performance perspective.

An advantage exists, therefore, for a supply valve for a pneumatically-operated gas demand apparatus which is simple in design, easily fabricated and assembled and resistant to gas leakage.

OBJECTS AND SUMMARY OF THE INVENTION

An object of the present invention is to provide a supply valve and diaphragm for a pneumatically-operated gas demand apparatus of a type which is coupled in interruptible fluid communication between a recipient/patient and at least one source of pressurized respiratory gas such as oxygen and which is operable to control delivery of oxygen or other respiratory gas to the recipient/patient as the recipient inhales and exhales while minimizing wastage of the respiratory gas.

Another object of the present invention is to provide a supply valve and diaphragm for a pneumatically-operated gas demand apparatus which is compact, simple in design, leak resistant and which may be constructed easily and cost effectively.

Accordingly, a supply valve and diaphragm for a pneumatically-operated gas demand apparatus of the present invention is hereinafter described. A pneumatically-operated gas demand apparatus is typically coupled in interruptible fluid communication between a recipient (or patient) and a first source of a pressurized first gas and is adapted for controlling delivery of the first gas to the recipient as the recipient inhales and exhales. In its broadest form, such apparatus, like that disclosed in U.S. Pat. No. 5,666,945 to Davenport, includes a supply valve and a sensing valve. The supply valve includes a supply valve housing and a flexible first diaphragm member. The supply valve housing defines a first interior chamber formed therein. The first diaphragm member is disposed within the first interior chamber and is connected to the supply valve housing in a manner to divide the first interior chamber into a supply chamber region and a control chamber region. The supply chamber region is in interruptible fluid communication with and between the first source of the first gas and the recipient and the control chamber region is in continuous fluid communication with either the first source of pressurized gas or a second source of a pressurized second gas. The first diaphragm member is operative to hermetically seal the supply chamber region and the control chamber region from one another and is operative to move between a flow-blocking position and a flow-supplying position.

The sensing valve includes a sensing valve housing and a flexible second diaphragm member. The sensing valve housing defines a second interior chamber formed therein. The second diaphragm member is disposed within the second interior chamber and is connected to the sensing valve housing in a manner to divide the second interior chamber into a venting chamber region and a sensing chamber region. The venting chamber region is in interruptible fluid communication with and between the control chamber region of the first interior chamber of the supply valve and an ambient air environment and the sensing chamber region is in continuous fluid communication with the recipient. The second diaphragm member is operative to hermetically seal the venting chamber region and the sensing chamber region from one another and is responsive, when the recipient inhales and exhales, to move between a flow-stopping position and a flow-causing position. When the recipient inhales, the second diaphragm member is in the flow-causing position thereby causing either pressurized first gas or second gas to flow from the control chamber region, through the venting chamber region and into the ambient air environment which, in turn, causes the first diaphragm member to be in the flow-supplying position thereby delivering the first gas from the first source of pressurized first gas to the recipient. When the recipient exhales, the second diaphragm member is in the flow-stopping position thereby preventing gas flow from the control chamber region, through the venting chamber region and into the ambient air environment which, in turn, causes the first diaphragm member to be in the flow-blocking position thereby preventing delivery of the first gas to the recipient.

The pneumatically-operated gas demand apparatus also normally includes a regulator mechanism disposed between and in interruptible fluid communication with the first source of the first gas and the supply chamber region of the supply valve. The regulator mechanism, like that disclosed in U.S. Pat. No. 5,666,945 to Davenport, can be adjusted and preferably comprises a regulator housing, a flexible regulator diaphragm and a valve assembly. The regulator housing defines a regulator chamber therein. The regulator diaphragm is disposed within the regulator chamber and is connected to the regulator housing in a manner to divide the regulator chamber into a vented regulator chamber region which is in continuous fluid communication with the ambient air environment and a supply regulator chamber region which is in interruptible fluid communication between the first source of pressurized first gas and the supply chamber region of the supply valve. The regulator diaphragm is operative to hermetically seal the vented regulator chamber region and the supply regulator chamber region from one another.

The valve assembly is operably connected to the regulator diaphragm and is disposed within the supply regulator chamber region. The valve assembly is operative between a closed condition and an opened condition. In the closed condition, an upstream portion of the supply regulator chamber region is in fluid isolation with a downstream portion of the supply regulator chamber region. In the opened condition, the upstream portion of the supply regulator chamber region is in fluid communication with the downstream portion of the supply regulator chamber region. The valve assembly is resiliently and yieldably biased against the regulator diaphragm in the closed condition and the regulator diaphragm is resiliently and yieldably biased against the valve assembly in the opened condition. When a first gas pressure of the first gas reaches a threshold gas pressure amount in the downstream portion of the supply regulator chamber region, the valve assembly is in the closed condition. When the first gas pressure is less than the threshold gas pressure amount, the valve assembly is in the opened condition.

When a plurality of pressurized gases are conveyed by the apparatus, the first gas and the second gas are oxygen and, therefore, the first gas and the second gas may be same. With the first and second gases being the same, then at least one gas source may comprise a first source and a second source of pressurized gas that could also, but not necessarily, be the same. The first gas and the second gas can be different from each other. If so, the first source and the second source must also be different from one another. The first gas and the second gas are selected from either different ones or the same one of a group of gases consisting of oxygen, nitrous oxide, air and other types of gases.

The present supply valve assembly avoids several of the fabrication and assembly steps required for currently existing pneumatically-operated gas demand apparatus supply valve designs. Furthermore, it results in a valve construction which less likely to leak pressurized respiratory gas than existing supply valves.

The present supply valve comprises a flexible supply valve diaphragm member disposed within an interior chamber of the supply valve housing. The supply valve diaphragm member divides the interior chamber into a supply chamber region and a control chamber region in a manner generally similar to that described in the Davenport patent. However, in lieu of intersecting first and second bored supply valve passageways variously sealed with O-rings, plugs or other sealing means, the present invention proposes a simplified supply valve construction. More particularly, the valve includes a diaphragm member having a radial projection or lobed portion and is received in a correspondingly shaped recess provided at the interface of first and second valve housing parts. The lobed portion of the diaphragm includes an aperture for enabling fluid communication between a first passageway provided in the first housing part and a second passageway provided in the second housing part. Rather than a bore extending radially outwardly to the circumferential surface of the second housing part which must be plugged or otherwise sealed after formation, the second passageway is preferably configured as a channel-like groove or slot which does hot extend to the periphery of the second housing part.

The shapes and dispositions of the diaphragm and the second passageway are such that, when the supply valve housing is assembled, no supplemental sealing means are required to effectuate proper sealing of the first and second passageways against gas leakage. The housing parts may be molded to include the desired diaphragm recess and second passageway configurations. Alternatively, the desired contours of these spaces may be achieved after formation of the housing parts using simple machining techniques and equipment known in the art.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE EXEMPLARY EMBODIMENTS

The present invention provides a supply valve and diaphragm for a pneumatically-operated gas demand apparatus of a type which is coupled in interruptible fluid communication between a recipient and a source of pressurized oxygen and is adapted for controlling delivery of oxygen to the recipient as the recipient inhales and exhales. Although the typical pneumatically-operated gas demand apparatus is well-suited for providing oxygen to a recipient/patient, one of ordinary skill in the art would appreciate that such apparatus can also be adapted and used to deliver other kinds of gases to recipients such as nitrous oxide. Further, the present supply valve and diaphragm may be used with pneumatically-operated gas demand apparatus such as, for example, that disclosed in the Davenport patent which can deliver and operate with either a single gas such as oxygen or two gases such as oxygen, or inexpensive compressed air, other types of gases. It will be further understood that the present supply valve may be used in an intermittent gas delivery device for a nebulizer.

Figure 1:
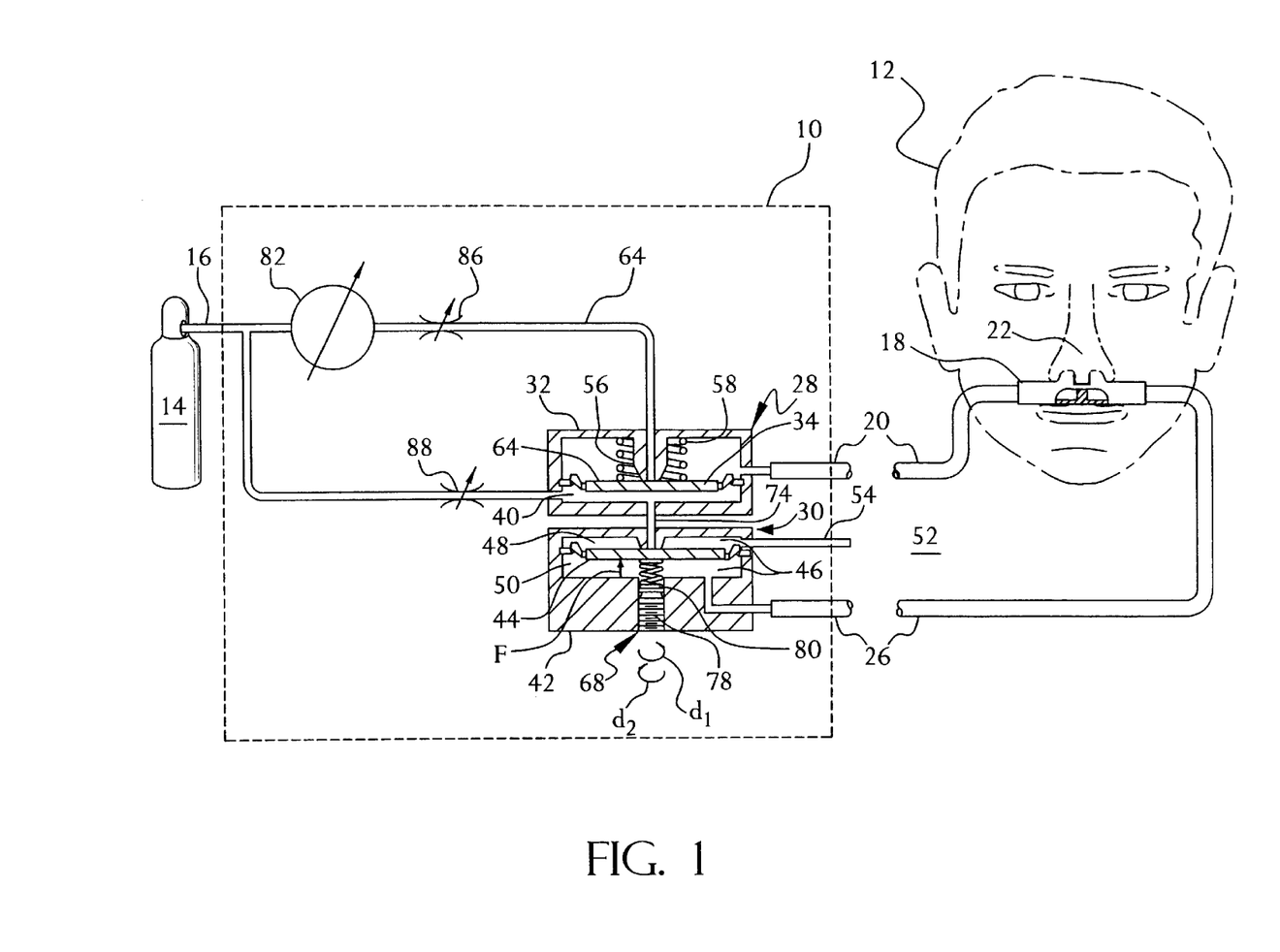
FIG. 1 is a partial schematic, partial elevational view in cross-section of a conventional pneumatically-operated gas demand apparatus shown coupled between and in fluid communication with a source of pressurized gas and a recipient with a supply valve in a flow blocking position and a sensing valve in a flow-stopping position as a result of the recipient exhaling.
Figure 2:
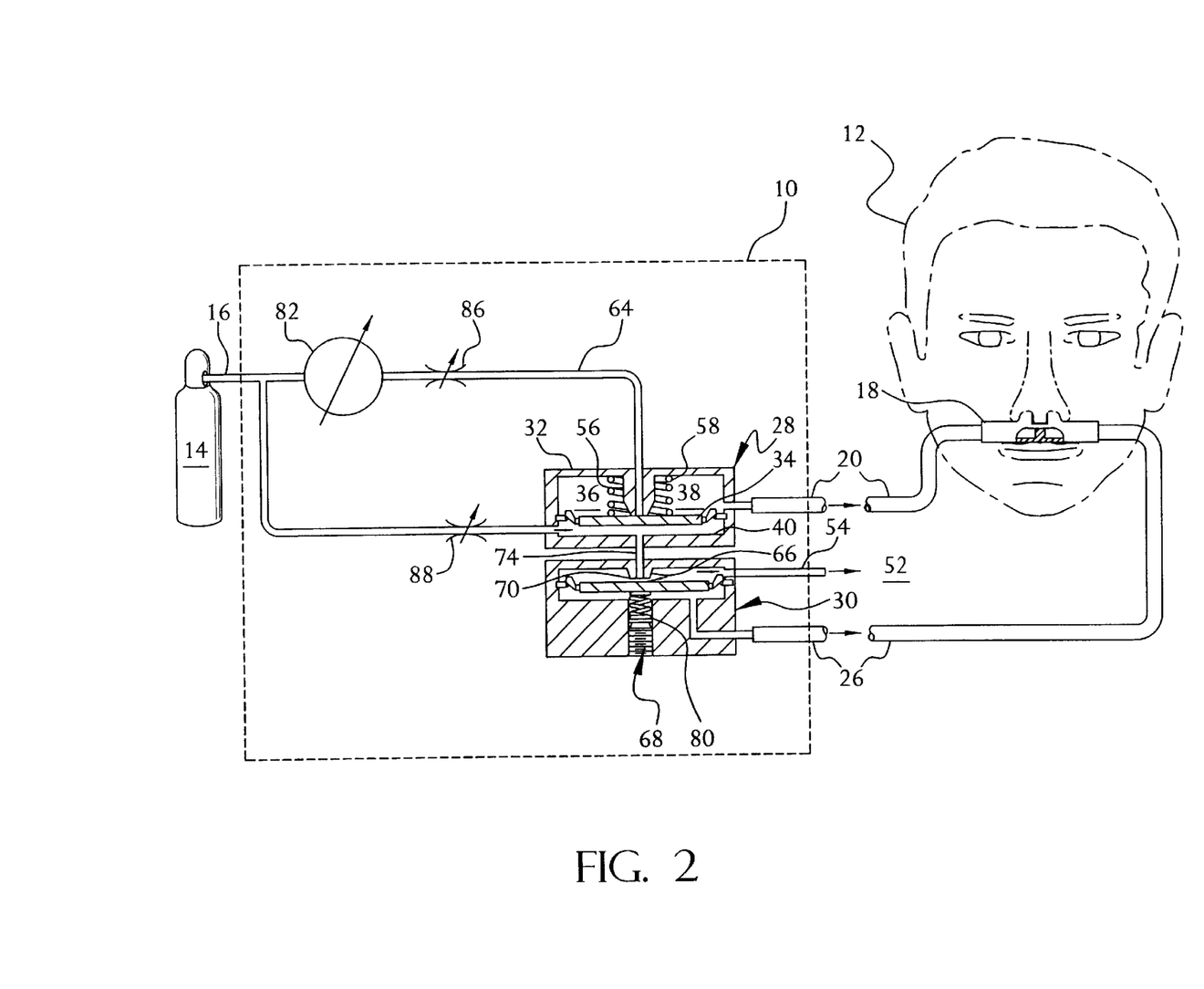
FIG. 2 is a view of the apparatus of FIG. 1 with the supply valve in a flow-supplying position and the sensing valve in a flow-causing position as a result of the recipient exhaling.

As generally introduced in FIGS. 1 and 2, a conventional pneumatically-operated gas demand apparatus 10 is coupled in interruptible fluid communication between a recipient 12 and at least one source 14 of pressurized respiratory gas such as oxygen. Conventional tubing 16 interconnects pneumatically-operated gas demand apparatus 10 to source 14 and a partitioned, nasal cannula assembly 18 interconnects pneumatically-operated gas demand apparatus 10 and recipient 12. A dual-lumen, nasal cannula assembly (not shown) can also be employed and is well known in the art and no additional explanation thereof is deemed necessary to practice the present invention. A first lumen 20 of a dual-lumen, nasal cannula assembly 18 is connected between pneumatically-operated gas demand apparatus 10 and recipient 12 to conduct oxygen to a nose 22 of the recipient. A second lumen 26 is connected between pneumatically-operated gas demand apparatus 10 cannula 18 to act as a conduit so that inhalation pressure and exhalation pressure to and from recipient 12 can be conveyed to and from pneumatically-operated gas demand apparatus 10. As a result, pneumatically-operated gas demand apparatus 10 is adapted for controlling delivery of gaseous oxygen to recipient 12 as the recipient inhales and exhales.

Again, with reference to FIGS. 1 and 2, pneumatically-operated gas demand apparatus 10 comprises a supply valve 28 and a sensing valve 30. Supply valve 28 includes a supply valve housing 32 and a flexible first diaphragm member 34. Supply valve housing 32 defines a first interior chamber 36 which is formed therein. Flexible first diaphragm member 34 is disposed within first interior chamber 36 and is connected to supply valve housing 32 in a manner to divide first interior chamber 36 into a supply chamber region 38 and a control chamber region 40. Supply chamber region 38 is in interruptible fluid communication with and between source 14 of the pressurized oxygen and recipient 12. Throughout the present description, the phrase, "interruptible fluid communication" is used and, by way of example only, "interruptible fluid communication" means that sometimes supply chamber region 38 is in fluid communication with source 14 while at other times supply chamber region 38 is not in fluid communication with source 14. Control chamber region 40 is in continuous fluid communication with source 14 of pressurized oxygen. First diaphragm member 34 is operative to hermetically seal supply chamber region 38 and control chamber region 40 from one another. Additionally, first diaphragm member 34 is operative to move between a flow-blocking position as shown in FIG. 1 and a flow-supplying position as shown in FIG. 2.

Sensing valve 30 includes a sensing valve housing 42 and a flexible second diaphragm member 44. Sensing valve housing 42 defines a second interior chamber 46 which is formed therein. Second diaphragm member 44 is disposed within second interior chamber 46 and is connected to sensing valve housing 42 in a manner to divide second interior chamber 46 into a venting chamber region 48 and a sensing chamber region 50. Venting chamber region 48 is in interruptible fluid communication with and between control chamber region 40 of first interior chamber 36 of supply valve 28 and an ambient air environment 52 through a bleed conduit 54. Sensing chamber region 50 is in continuous fluid communication with recipient 12.

Second diaphragm member 44 is operative to hermetically seal venting chamber region 48 and sensing chamber region 50 from one another. Further, second diaphragm member 44 is responsive when recipient 12 inhales and exhales by moving between a flow-stopping position as shown in FIG. 1 and a flow-causing position as shown by FIG. 2. As best shown in FIG. 3, when recipient 12 inhales, second diaphragm member 44 is in the flow-causing position thereby causing oxygen (represented by the single solid line arrows) to flow from control chamber region 40, through venting chamber region 48 and into ambient air environment 52. In turn, second diaphragm member 44 being in the flow-causing position causes first diaphragm member 34 to be in the flow-supplying position thereby delivering oxygen (represented by dashed arrows) from source 14 of pressurized oxygen to recipient 12. As shown in FIG. 2, when recipient 12 exhales, second diaphragm member 44 is in the flow-stopping position thereby preventing oxygen to flow from control chamber region 40, through venting chamber region 48 and into ambient air environment 52 which, in turn, causes first diaphragm member 34 to be in the flow-blocking position thereby preventing delivery of oxygen to recipient 12.

Supply valve 28 includes a supply tube stem 56 and a supply valve spring 58. Supply tube stem 56 is disposed within supply chamber region 38 of supply valve 28 and has a supply seat 60 defining a supply opening of a tube stem conduit 64. Tube stem conduit 64 provides fluid communication into supply chamber region 38. Supply seat 60 is sized and adapted to removably contact a blocking side of first diaphragm member 34 in a fluid-tight relation when supply valve 28 is in the flow-blocking position as shown in FIG. 1. Also, as shown in FIG. 2, the first diaphragm member 34 is in a spaced-apart, facially-opposing relationship with the supply opening of the tube stem conduit 64 when supply valve 28 is in the flow-supplying position. Supply valve spring 58 is disposed within supply chamber region 38 and surrounding supply tube stem 56. Supply valve spring 58 is operative to yieldably urge first diaphragm member 34 into the flow-supplying position.

Sensing valve 30 includes a sensing valve seat member 66 and a sensing valve adjustment assembly 68. Sensing valve seat member 66 is disposed in and extends into venting chamber region 48. Sensing valve seat member 66 has a sensing valve seat 70 which defines a flow opening into a supply valve conduit 74. Supply valve conduit 74 provides fluid communication into venting chamber region 48 of sensing valve 30. Sensing valve seat 70 is sized and adapted to removably contact second diaphragm member 44 in a fluid-tight relation when sensing valve 30 is in the flow-stopping position as shown in FIG. 1. The flow opening of supply valve conduit 74 is in a spaced-apart, facially-opposing relationship from second diaphragm member 44 when sensing valve 30 is in the flow-causing position as shown in FIG. 2.

Sensing valve adjustment assembly 68 includes a set screw 78 and a sensing valve spring 80. Set screw 78, threadably mounted into sensing valve housing 42, extends into sensing chamber region 50 and is accessible exteriorly of sensing valve housing 42. Sensing valve spring 80 is disposed within sensing chamber region 50 and in contact with and between set screw 78 and second diaphragm member 44. Sensing valve spring 80 imparts a yieldable tension force "F", shown in FIG. 1, to second diaphragm member 44 against sensing valve seat 70 to resiliently bias second diaphragm member 44 into the flow-stopping position. As commonly known in the art, turning set screw 78 in a first direction "$d_1$" decreases tension force "F" and turning set screw 78 in a second direction "$d_2$" opposite the first direction "$d_1$" decreases the tension force "F".

Pneumatically-operated gas demand apparatus 10 includes a conventional regulator mechanism 82 (drawn symbolically), a supply orifice element 86 (drawn symbolically) and a pilot orifice element 88 (drawn symbolically). Regulator mechanism 82 would be disposed between and in interruptible fluid communication with source 14 of pressurized oxygen and supply chamber region 38 of supply valve 28. If constructed in accordance with the Davenport patent, apparatus 10 would also include an unillustrated bolus chamber structure defining an internal chamber therein. The bolus chamber structure would be disposed between and in fluid communication with regulator mechanism 82 and supply chamber region 38 of supply valve 28. If the bolus chamber structure is present, supply orifice element 86 would be disposed between regulator mechanism 82 and the bolus chamber structure. Pilot orifice element 88 is disposed between source 14 of the pressurized oxygen and control chamber region 40 of supply valve 28. By way of example and not limitation, pilot orifice element 88 and supply orifice element 86, as reflected by the symbolic drawings, are of an adjustable, variable orifice type which are commonly known in the art. The purpose of the bolus chamber structure is enable apparatus 10 to deliver a high-flow burst of oxygen or other pressurized respiratory gas upon initiation of inhalation in order to enrich the air in the patient's airway with the delivered respiratory gas.

Figure 3A:
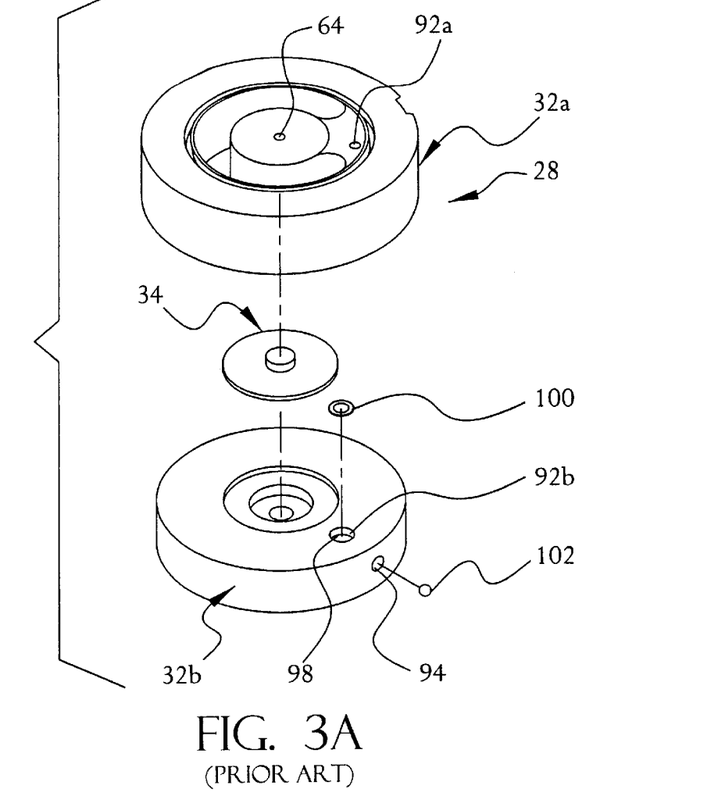
FIG. 3A is an exploded view of a conventional supply valve for a pneumatically operated gas demand apparatus.
Figure 3B:
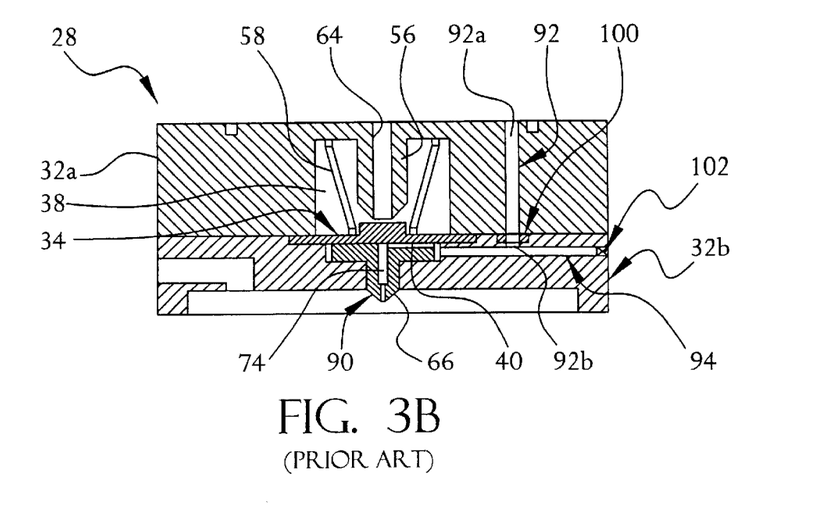
FIG. 3B is an elevational cross-section view, in assembled condition, of the supply valve of FIG. 3A.

FIGS. 3A and 3B collectively depict in greater detail the structure of supply valve 28. More particularly, the supply valve housing is comprised of first and second housing parts 32a and 32b which may alternatively be referred to as a pilot plate and a sense nozzle plate, respectively. The flexible diaphragm member 34, supply tube stem 56, supply valve spring 58 and tube stem conduit are arranged as described hereinabove in connection with FIGS. 1 and 2.

The sensing valve seat member 66 is provided at the lower end of a sense nozzle 90 which includes therein supply valve conduit 74. Control chamber region 40 is supplied with pressurized respiratory gas from source 14 through first and second cooperating passageways 92 and 94 respectively provided in housing parts 32a and 32b. First passageway 92 is comprised a first portion 92a provided in housing part 32a and a second portion 92b provided in housing part 32b. After formation of the housing part 32a, 32b, both housing parts must be drilled or bored to produce first passageway 92. The second housing part 32b is also radially drilled from its outer circumferential surface inwardly to produce the second passageway 94 which intersects the first passageway 92. Either first housing part 32a or, as illustrated, second housing part 32b must also counter-bored to provide a receptacle 98 for receiving an elastomeric sealing means 100 such as a conventional O-ring or the like. The purpose of O-ring 100 is to resist gas leakage through the abutting faces of housing parts 32a, 32b that may escape from the juncture the first and second portions 92a, 92b of first passageway 92.

Second passageway 94 must be closed by a plug 102 to seal the second passageway from the ambient atmosphere. Plug 102 may be a metal ball or tapered metal plug pressed into the second passageway, a threaded self-sealing plug or other suitable means sealing means. The many parts and fabrication and assembly steps complicate construction of supply valve 28. Moreover, both the first and second passageways 92, 94 require supplemental sealing means to resist leakage of pressurized respiratory gas from supply valve. Manufacture and installation of these additional parts further increases cost and complexity of assembly of the valve. Additionally, their very presence in the supply valve 28 creates multiple sites from which gas may leak from the valve during operation.

Figure 4A:
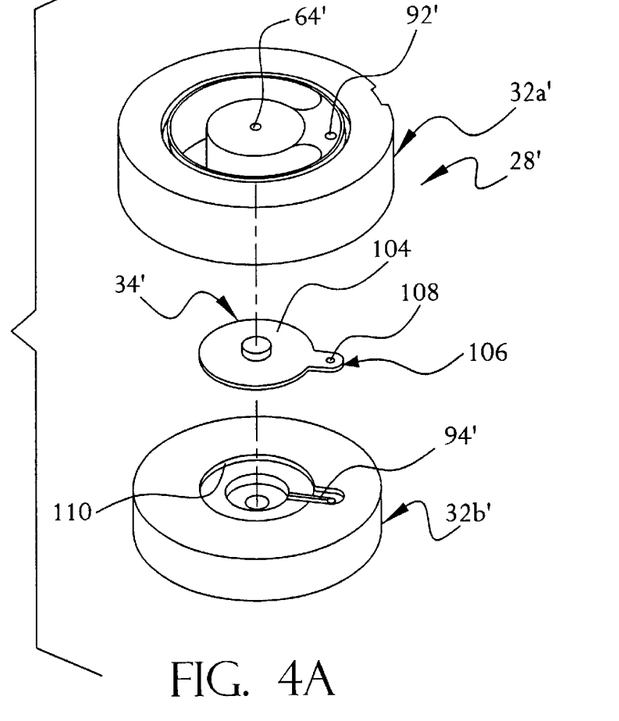
FIG. 4A is an exploded view of a supply valve constructed according to the present invention.
Figure 4B:
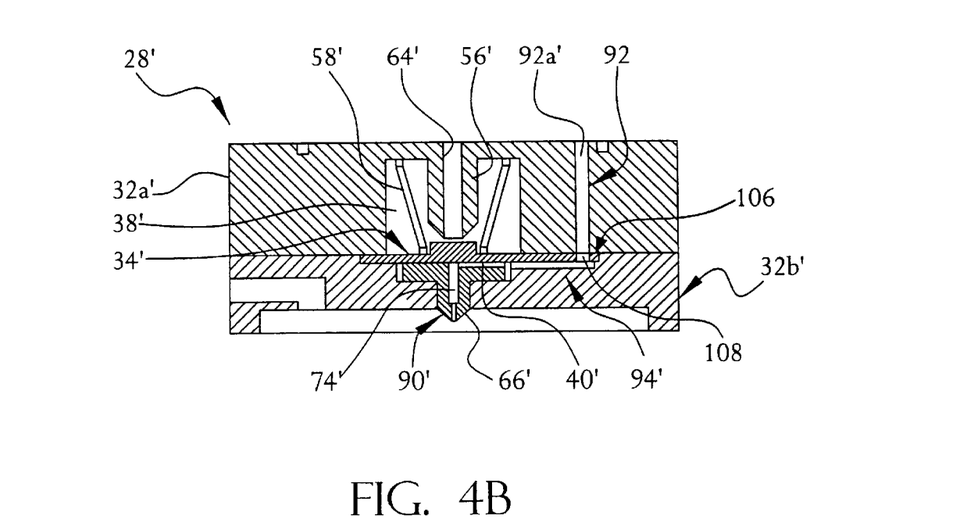
FIG. 4B is an elevational cross-section view, in assembled condition, of the supply valve of FIG. 4A.

FIGS. 4A and 4B represent a supply or pilot valve 28' constructed in accordance with a presently preferred embodiment of the instant invention. Supply valve 28' includes a housing comprised of first and second housing parts 32a' and 32b' which may alternatively be referred to as a pilot plate and a sense nozzle plate, respectively. Supply valve 28' further includes a flexible diaphragm member 34' which may be formed from rubber, silicone rubber, EDPM, neoprene or any elastomeric material capable of being formed to the desired shape and functioning as described herein. Diaphragm member 34' includes a central sealing portion 104 of preferably, although not necessarily, general circular configuration. When flexible diaphragm member is disposed in an interior chamber of the supply valve housing as shown in FIG. 4B, the central sealing portion 104 of the diaphragm member 34' divides the interior chamber into a supply chamber region 38' and a control chamber region 40'. A supply valve spring 56' is disposed in supply chamber region 38' and surrounding a supply tube stem 58'. Supply valve spring 56' is operative to yieldably urge the central sealing portion 104 of diaphragm member 34' into a flow supplying position similar to first diaphragm member 34 shown in FIG. 2.

In all other respects, supply chamber region 38', control chamber region 40' and elements 56', 58', 64', 66', 74' and 90' of supply valve 28' are preferably substantially similar in construction and function to their counterparts in FIGS. 3A and 3B and thus will not be described in greater detail herein except where necessary to provide the reader with a proper understanding of the invention.

According to the present invention, the first and second housing parts 32a', 32b' include cooperating first and second passageways 92' and 94', respectively. First and second passageways 92' 94' provide fluid communication from supply valve 28' to an unillustrated sensing valve (the upper housing part of which may be coincidental with second housing part 32b' and which may be similar in construction and function to sensing valve 30 described above) or a sense tube such as sense tube 516 described hereinafter in connection with the intermittent gas delivery device 510 shown in FIG. 5. First and second passageways 92', 94' differ from first and second passageways 92, 94 (FIGS. 3A and 3B) in several respects.

For instance, first passageway 92' is formed as a single bore extending only through first housing part 32a' whereas first passageway 92 includes first and second portions 92a, 92b provided in both first housing part 32a and second housing part 32b. With the first passageway 92' formed as a single bore in the first housing part 32a', the need to provide a receptacle and sealing means such as element 98 (FIG. 3A) and sealing means 100 (FIGS. 3A and 3B) to effectuate sealing of the juncture of a dual-portion first passageway such as passageway 92 is eliminated.

Furthermore, unlike second passageway 94 of supply valve 28 which extends to the circumference of the second housing part 32b, second passageway 94' is configured as a channel which lies entirely within the periphery of the second housing part 32b'. Since the second passageway 94' does not reach the circumferential exterior of the second housing part 32b', no supplemental plug or other means, such as plug 102 of FIGS. 3A and 3B, is required to seal the second passageway 94' from the ambient atmosphere.

According to the present invention, in addition to central sealing zone 104 the diaphragm member 34' preferably includes means integral with the central sealing portion for enabling fluid communication between first and second passageways 92', 94' and for sealing the first and second passageways against gas leakage. These means, identified generally by reference numeral 106 in FIG. 4A, preferably comprise a projection or lobed portion extending outwardly from the peripheral edge of central sealing zone 104. Means 106 includes an aperture 108 for permitting respiratory gas to flow from first passageway 92' to second passageway 94'. Valve diaphragm 34' may be received in a correspondingly-shaped recess 110 provided in the first housing part 92' or, as illustrated and preferred, second housing part 94'.

The housing parts 92', 94' may be molded to include the desired diaphragm recess 110 and second passageway 94' configurations. Alternatively, the desired contours of these spaces may be achieved after formation of the housing parts 92', 94' using simple machining techniques and equipment known in the art. As best seen in FIG. 4B, the cooperating shapes of the housing parts 32a', 32b' and diaphragm member 34' (including means 106) produces a supply valve which is simple and economical to fabricate and assemble, and which also is highly resistant to pressurized respiratory gas leakage during operation, versus supply valves heretofore known in the art.

Figure 5:
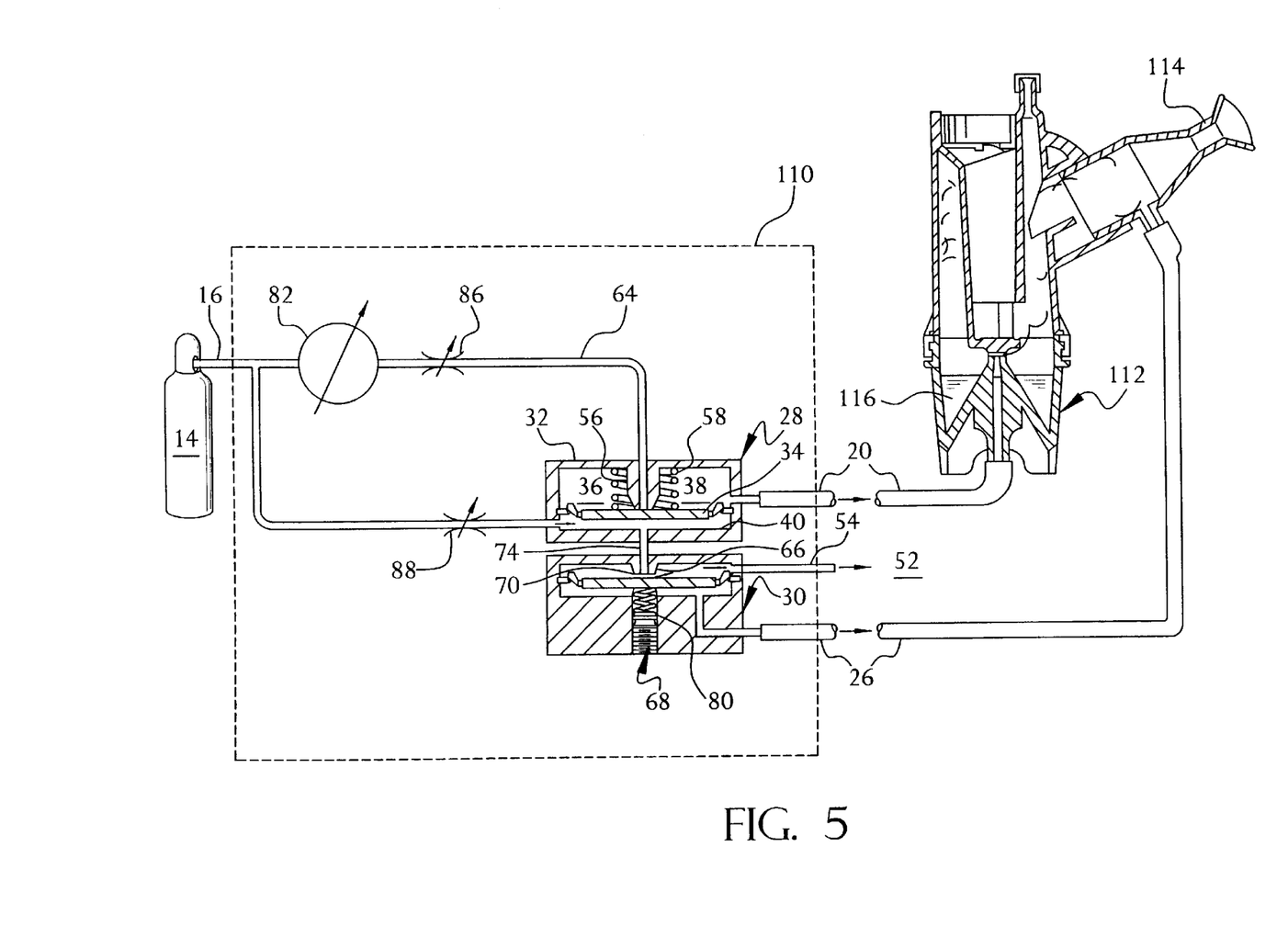
FIG. 5 is a partial schematic, partial elevational view of a supply valve according to the present invention as incorporated into an intermittent gas delivery device used in combination with a nebulizer.

As shown in FIG. 5, it is also contemplated that components of pneumatically-operated gas demand apparatus of FIGS. 1 and 2 can be combined with other components to construct an intermittent gas delivery device 110. Such intermittent gas delivery device could be utilized, for example, with a nebulizer such as the one described in U.S. Pat. No. 5,584,285 to Chua, et al. Other nebulizers are commonly known in the art and can be employed if equipped with an inhalation sensing structure or supplemental sensing apparatus. The elements of device 110 that bear like or similar reference numerals to elements of apparatus 10 illustrated in FIGS. 1 and 2 may be considered structurally and functionally equivalent to their counterparts in those figures and thus will not be described in detail in connection with FIG. 5 except where necessary to provide a proper understanding of the invention.

Intermittent gas delivery device 110 is preferably connected in fluid communication between source 14 of pressurized gas, such as air or oxygen, and a nebulizer 112 via first and second lumens 20,26 in the manner illustrated. Inhalation by the user on the mouthpiece 114 of nebulizer 112 causes supply valve 28 and sensing valve 30 to provide gas flow to the nebulizer 112. During inhalation nebulizer 112 generates a fine-mist plume of a medicament-containing aerosol by virtue of pressurized gas entering the nebulizer through first lumen 20 and aersolizing liquid medicament 116 contained in the nebulizer. Exhalation by the user causes supply valve 28 and sensing valve 30 to cease gas flow to nebulizer 122, thereby halting aerosolization of medicament 116. So constructed, intermittent gas delivery device 110 makes far more efficient use of medicament 118 than presently known continuous flow nebulizer apparatus that continuously aerosolize the medicament and wastefully vent the aerosolized medicament during the user's exhalation cycle.

Although the invention has been described in detail for the purpose of illustration, it is to be understood that such detail is solely for the purpose and that variations can be made therein by those skilled in the art without departing from the spirit and scope of the invention except as it may be limited by the claims.

What is claimed is:

1. A flexible diaphragm member adapted for disposition in a chamber formed between first and second housing parts of a valve housing wherein the first and second housing parts include respective first and second cooperating fluid passageways, said diaphragm member comprising:

a central sealing portion for dividing the chamber into a supply chamber region and a control chamber region; and means integral with said central sealing portion for enabling fluid communication between the first and second fluid passageways, said means integral with said central sealing portion comprising a projection extending outwardly from a peripheral edge of said central sealing portion, said projection including an aperture for permitting communication between the first and second fluid passageways.

2. The diaphragm member of claim 1 wherein said means integral with said central sealing portion is configured to seal said first and second passageways against leakage.

3. A valve comprising:

a valve housing including first and second housing parts defining a chamber, said first and second housing parts including respective first and second cooperating fluid passageways; and a flexible diaphragm member disposed in said chamber, said diaphragm member comprising:

a central sealing portion for dividing said chamber into a supply chamber region and a control chamber region; and means integral with said central sealing portion for enabling fluid communication between said first and second fluid passageways, said means integral with said central sealing portion comprising a projection extending outwardly from a peripheral edge of said central sealing portion, said projection including an aperture for permitting communication between said first and second passageways.

4. The value of claim 3 wherein said means integral with said central sealing portion is configured to seal said first and second passageways against leakage.

5. The valve of claim 3 wherein one of said first and second housing parts includes a recess for receiving said diaphragm member, said recess corresponding in shape to said central sealing portion and said projection.

6. The valve of claim 3 wherein said second fluid passageway comprises a channel lying entirely within the periphery of said second housing part.

7. A pneumatically-operated gas demand apparatus adapted to be in intermittent fluid communication between at least one source of pressurized respiratory gas and a recipient and comprising the valve of claim 3.

8. An intermittent gas delivery device adapted to be in intermittent fluid communication between a source of pressurized respiratory gas and a recipient and comprising the valve of claim 3.

* * * * *